United States Patent [19]
Costello

[11] Patent Number: 5,874,094
[45] Date of Patent: Feb. 23, 1999

[54] CREAM FORMULATION FOR TOPICAL APPLICATION

[76] Inventor: Jeremiah Costello, 905 West Chester Dr., Wexford, Pa. 15090

[21] Appl. No.: 906,505

[22] Filed: Aug. 5, 1997

[51] Int. Cl.⁶ ..................................................... A61K 7/48
[52] U.S. Cl. ........................................... 424/401; 424/70.1
[58] Field of Search .................................. 424/401, 70.1, 424/195

[56] References Cited

U.S. PATENT DOCUMENTS

| | | | |
|---|---|---|---|
| 5,244,665 | 9/1993 | Natraj | 424/401 |
| 5,702,691 | 12/1997 | Ichnose | 424/70.1 |

*Primary Examiner*—Thurman K. Page
*Assistant Examiner*—D. Faulkner
*Attorney, Agent, or Firm*—James Ray & Associates

[57] ABSTRACT

A cream formulation for topical application to an external portion of a human body. A one ounce preparation of such cream formulation includes active ingredients consisting essentially of a predetermined weight of an aloe vera gel compound present in the topical formulation generally in a weight range of between about 3 grams and about 10 grams. A predetermined weight of a preselected zinc compound present in the topical formulation generally in a weight range of between about 0.4 gram and about 1.5 grams. A predetermined weight, expressed as IU, of vitamin E present in the topical formulation generally in a weight range of between about 200 IU and about 9000 IU. The balance of such one ounce preparation of the topical formulation being made up of water, organic solvents, carriers and emollients.

9 Claims, No Drawings

CREAM FORMULATION FOR TOPICAL APPLICATION

FIELD OF THE INVENTION

The present invention relates, in general, to formulations utilized as topical applications to the skin for a variety of skin disorders and, more particularly, the present invention relates to a cream formulation which will exhibit enhanced soothing effects when utilized as a topical application to the skin for such variety of skin disorders and, still more specifically, this invention relates to a cream formulation which may provide temporary relief of minor pain.

BACKGROUND OF THE INVENTION

Prior to the conception and subsequent development of the present invention, as is generally well known in the prior art, there are a variety of skin creams and lotions today which are used to soften skin, repair lesions, combat dryness and redness and reduce swelling and roughness in irritated skin. There are also a variety of creams or ointments that are used to reduce the itch from poison ivy and insect bites.

Virtually everyone has endured the discomfort of dry, chapped hands at one time or another or experienced rough, sore hands with cracks at every joint on the fingers. Not only hands but other external portions of the body are susceptible to dryness, irritation and lesions. Despite all of the products on the market, there is still a need for a topical product which will not only soften and moisturize dry and chapped hands but also provide healing for skin cracks and lesions.

In the area of topical creams and ointments there is a further need for a product which can be effective in the treatment of and prevention of cold sores caused by enveloped viruses such as the herpes simplex virus. Additionally, it would be useful to have a product that could be effective in treating shingles caused by herpes zoster and it's cousin chicken pox caused by herpes varicella. All three of these virus caused manifestations present unique problems in their treatment.

Another particular and agonizing problem is that of post-herpetic neuralgia (PHN). PHN is an ailment caused by having had herpes zoster. Up to 50% of elderly patients that have had shingles may develop PHN. As our life span increases and the number of elderly increase, correspondingly, the number of elderly who contract shingles increases also. An effective treatment for this disorder is thus becoming more and more important.

An important fact that must be understood with relation to PHN is that PHN is not a continuation of herpes zoster (shingles). It is a separate condition that is caused by having had shingles. There is evidence to suggest that PHN is not viral in nature, however, nothing conclusive has been established in this regard. PHN may be defined as pain that continues at the site of shingles beyond a period of 1–3 months. Incidence of PHN in young patients is rare, even up to 40 years of age.

However, in a study by the Pain Research Institute at the Walton Hospital, Liverpool, England, it was found that half of the patients who contracted shingles at age 60 developed PHN and the percentage increased to 75% for those diagnosed as having shingles at age 70 or older. As the average life span continues to increase and the number of elderly increases, the incidence is increasing at a very rapid rate.

Thus, there are many in the world that are eagerly waiting for a medication which could be used in the treatment of a variety of skin ailments, as well as for viral skin infections and the very painful and relatively untreatable post-herpetic neuralgia.

Use of a purified extract from the leaves of the plant *Eriobotrya japonica* for the inhibition of the cytopathogenic effects of herpes simplex virus is described in U.S. Pat. No. 5,279,827. The method of preparation and purification of the extract is described in U.S. Pat. No. 5,137,722 and U.S. Pat. No. 5,279,827. The method of preparation and purification of the extract and the use of the purified extract for the inhibition of viruses described in these patents is incorporated herein by reference thereto.

SUMMARY OF THE INVENTION

In a first aspect of the present invention there is provided a cream formulation for topical application to an external portion of a human body. The active ingredients of a one ounce preparation of such cream formulation, in this embodiment, consists essentially of a predetermined weight of an aloe vera gel compound. Such predetermined weight of such aloe vera gel compound being present in the cream formulation generally in a range of between about 3 grams and about 10 grams. The cream formulation also includes a predetermined weight of a preselected zinc compound. Such predetermined weight of such zinc compound being present in the cream formulation generally in a range of between about 0.4 grams and about 1.5 gram. The active ingredients further contain a predetermined weight of a preselected vitamin E. Such predetermined weight of such preselected vitamin E being present in the cream formulation generally in a range (expressed as International Units) of between about 200 IU and about 9000 IU. The balance of such one ounce preparation of the cream formulation being made up of water, organic solvents, carriers and emollients.

In another embodiment of the invention the above described cream formulation further includes a purified extract of the leaves of the plant *Eriobotrya japonica*.

OBJECTS OF THE INVENTION

It is, therefore, one of the primary objects of the present invention to provide a cream formulation for topical application which will generally be more effective as a treatment for dry, chapped, cracked and irritated skin than prior art type cream formulations.

It is also an object of the present invention to provide a cream formulation for topical application which will generally be more effective as a treatment for reducing the itch of poison ivy and insect bites than prior art type cream formulations presently being used for these afflictions.

It is still another object of the present invention to provide a cream formulation for topical application which in certain cases will be more effective as a treatment for the manifestation of herpes simplex, herpes zoster and herpes varicella than treatments presently being used.

Yet, it is another object of the present invention to provide a cream formulation for topical application which possesses the capability of being more effective as a treatment for post-herpetic neuralgia.

In addition to the number of objects and advantages of the present invention which have been discussed above, it should be noted that various other objects and advantages of the topical formulation for a variety of applications will become more readily apparent to those persons who are particularly skilled in the art from the following more detailed description of such invention.

BRIEF DESCRIPTION OF THE PRESENTLY PREFERRED AND VARIOUS ALTERNATE EMBODIMENTS OF THE PRESENT INVENTION

The cream formulation in a first embodiment of the instant invention is a formulation to be applied to the external portion of a human body for treatment of a variety of skin ailments including dry, chapped, cracked, irritated skin, minor burns and even skin lesions. Such cream formulation may, also, be used as an effective treatment for reducing the itch of poison ivy and insect bites, including mosquito bites.

In an alternative embodiment of the invention such cream formulation is formulated to be used in certain cases as a treatment for manifestations of herpes simplex, herpes zoster and herpes varicella and such cream formulation is also formulated to be used in the treatment of post-herpetic neuralgia.

A one ounce preparation of the cream formulation includes active ingredients consisting essentially of a predetermined weight of an aloe vera gel compound. Such predetermined weight of the aloe vera gel compound is present in the topical formulation generally in a range of between about 3 grams and about 10 grams. Such cream formulation also includes a predetermined weight of a preselected zinc compound. Such predetermined weight of the zinc compound is present in the cream formulation generally in a range of between about 0.4 gram and about 1.5 grams.

The cream formulation further includes a predetermined weight of vitamin E, such predetermined weight of such vitamin E is present in the cream formulation generally in a range expressed as International Units of between about 200 IU and about 9000 IU (between about 0.19 gram and about 9.25 grams). The balance of such one ounce preparation of the cream formulation is made up of water, organic solvents, carriers and emollients.

In another alternate embodiment of the invention, a purified extract from the cells of the plant *Eriobotrya japonica* is added to the formulation generally in a range of between about 3 mg and about 15 mg. A very pure extract, as it becomes available, could be added to the formulation in microgram quantities.

Prior to the preparation of the cream formulation, aloe vera gel is first blended with water, mineral oil and emulsifiers in order to prepare a solution which makes the blending of the active ingredients easier. Such a solution is made to contain approximately 30 to 35 percent aloe vera. There are also aloe vera solutions which are commercially available which may be used as the source of aloe vera gel instead of preparing such solution.

Further, in an embodiment of the invention for the preparation of such cream formulation for topical application, it is presently preferred that the zinc compound be zinc oxide. In the preparation of the cream formulation of the instant invention a commercial blend containing zinc oxide is used as a source for such zinc compound. Such commercial blend contains approximately 20% zinc oxide in a mineral oil, beeswax and petroleum base.

To prepare a one ounce portion of the cream formulation in a first embodiment of the invention, between about 2 grams and about 7.5 grams of such blend containing zinc oxide is added to a container. This addition provides between about 0.4 gram and about 1.5 grams of zinc oxide. The additions described below will all be based on the amount of zinc oxide and not the amount of the blend that is added to the topical cream formulation.

Next, between about 11 grams and about 30 grams of such prepared aloe vera solution is measured out, so as to provide between about 3 grams and about 10 grams of aloe vera in the cream formulation. From this measured out portion of the prepared aloe vera solution between about 3 grams and about 10 grams is added to the container including such blend containing zinc oxide and the ingredients are then mixed together.

Then, between about 200 IU and about 9000 IU (between about 0.19 gram and about 9.25 grams) of natural vitamin E (alpha-tocopherol) is added and the mixture again blended. Here it must be emphasized that it is important that natural vitamin E (D-alpha-tocopherol) be used and not a synthetic mixture which might contain large quantities of other forms of vitamin E, such as DL-alpha, or beta, gamma, delta and epsilon isomers of tocopherol. Small concentrations of these other forms of vitamin E will probably be present even in natural vitamin E, however, they will be present in only very small or trace quantities and it will be essentially D-alpha-tocopherol.

A second addition of between about 5 grams and about 9 more grams of the prepared aloe vera solution is then added and the cream formulation again mixed thoroughly. Finally, the remaining portion of the aloe vera solution is added and the cream formulation again thoroughly mixed. It must be mentioned that it is important to add vitamin E after the first two additions (i.e. addition of zinc oxide and the first aloe vera addition) because alpha-tocopherol is rather oily and tends to migrate to the sides of the container and is much more difficult to blend into the mixture if it is added earlier when there is less material in the container. As mentioned supra, it is again emphasized that the cream formulation be thoroughly blended.

Thus, in a one ounce (approximately 28 grams) preparation of a first embodiment of the invention such formulation contains between about 3 grams and about 10 grams of aloe vera, between about 200 IU and about 9000 IU (between about 0.19 gram and about 9.25 grams) of natural vitamin E (alpha-tocopherol) and between about 0.4 gram and about 1.5 grams of zinc oxide.

In a presently preferred embodiment of the invention such one ounce portion of such topical formulation contains between about 6 grams and about 8 grams of aloe vera, between about 0.6 gram and 10 about 0.8 gram of zinc oxide and between about 1000 IU and about 3000 IU (between about 0.9 gram and about 2.8 grams) of alpha-tocopherol.

Such a cream formulation as described in the first embodiment of the invention containing the active ingredients of aloe vera, zinc oxide and vitamin E has been used effectively when applied to the external portion of a human body for treatment of a variety of skin ailments including treatment for dry, chapped, cracked, irritated skin, minor skin burns and even skin lesions. Such a formulation has also been used as an effective treatment in reducing the itching of poison ivy and insect bites, including mosquito bites. Such a cream formulation has also been effective in treatment of manifestations caused by herpes simplex, herpes zoster, herpes varicella and even some cases of PHN.

In an alternate embodiment of the invention, a formulation is specifically prepared for the treatment of certain cases of post-herpetic neuralgia and is also effective in treating shingles, cold sores and chicken pox rash. The formulation remains basically the same as that described in the first embodiment above. The only significant difference is the addition of the extract from the leaves of the plant *Eriobotrya japonica*. In such a one ounce preparation as described above, between about 3 milligrams and about 15 milligrams of the extract are added. Because the addition of such extract is minor, there is no need to alter the concentrations of aloe vera, zinc oxide or vitamin E even if the extract is added in the 10 to 15 milligrams range.

In a more preferred embodiment of the invention, a one ounce portion of such topical formulation contains between about 6 mg and about 12 mg of the extract from the leaves of the plant *Eriobotrya japonica*.

The procedure for the extraction from the leaves of the plant *Eriobotrya japonica* and subsequent purification of such extract is found in U.S. Pat. No. 5,137,722 and U.S. Pat. No. 5,279,827. The use of the purified extract for the inhibition of the cytopathogenic effects of herpes simplex virus is further described in U.S. Pat. No. 5,279,827. The method of preparation and purification of the extract and the use of the purified extract for the inhibition of viruses described in these patents is incorporated herein by reference thereto.

In this embodiment of the invention such topical cream formulation could still be used to treat the other ailments mentioned above including dry, chapped, cracked or irritated skin, skin lesions, reducing the itch of poison ivy and insect bites and even for minor skin burns. However, the cost of such cream formulation will probably be somewhat higher.

It must be remembered, as in all treatments of an ailment such as PHN, that nothing is or has been even close to being 100% effective because there is still much to learn about this ailment. However, in the cases where this formulation was used with persons who had suffered with this disorder for at least four months or more, those who found that it relieved the pain far outnumbered those that found no relief or only marginal improvement. Again, since it may take a considerable period of time to verify that such pain is gone and not just in remission, there can be no certainty that pain might not return. However, anyone who has experienced the pain of PHN will gladly accept relief, even for a short period of time and even if the application may have to be repeated periodically.

In alternate embodiments of the invention in which the cream formulation contains increased levels of vitamin E the levels of aloe vera are correspondingly reduced. In an embodiment which contains between about 7000 IU and about 9000 IU of vitamin E, the addition of the aloe vera solution is correspondingly reduced to between about 15 grams and about 19 grams to compensate for the additional vitamin E. In such cream formulations, the zinc oxide content remains between about 0.4 gram and about 1.5 grams. Since less aloe vera solution and more vitamin E are used in this embodiment, greater care must be employed to insure a thoroughly blended cream formulation, particularly in the step involving the addition of vitamin E.

While a number of presently preferred and various alternative embodiments of the present invention have been described in detail above, various other adaptations and modifications of the cream formulation for topical application to an external portion of a human body may be made by those persons who are skilled in the relevant art without departing from either the spirit of the invention or the scope of the appended claims.

I claim:

1. A cream formulation for topical application to an external portion of a human body, a one ounce preparation of such cream formulation includes active ingredients consisting essentially of:
   (a) a predetermined weight of an aloe vera gel compound, said predetermined weight of said aloe vera gel compound being present in said cream formulation generally in a weight range of between about 3 grams and about 10 grams;
   (b) a predetermined weight of a preselected zinc compound, said predetermined weight of said preselected zinc compound being present in said cream formulation generally in a weight range of between about 0.4 gram and about 1.5 grams;
   (c) a predetermined weight, expressed as IU, of vitamin E, said predetermined weight of said vitamin E being present in said cream formulation generally in a weight range of between about 200 IU and about 9000 IU;
   (d) a predetermined weight of a purified extract from leaves of a plant *Eriobotrya japonica*, said predetermined weight of said purified extract from said leaves of said plant *Eriobotrya japonica* being present in said cream formulation generally in a weight range of between about 3 mg and about 15 mg; and
   (e) a balance of said one ounce preparation of said cream formulation being made up of water, organic solvents, carriers and emollients.

2. A cream formulation for topical application to an external portion of a human body, according to claim 1, wherein said preselected zinc compound is zinc oxide.

3. A cream formulation for topical application to an external portion of a human body, according to claim 1, wherein said vitamin E is essentially alpha-tocopherol.

4. A cream formulation for topical application to an external portion of a human body, according to claim 1, wherein said predetermined weight of said aloe vera gel compound present in said cream formulation is generally in a weight range of between about 6 grams and about 8 grams.

5. A cream formulation for topical application to an external portion of a human body, according to claim 1, wherein said predetermined weight of said preselected zinc compound present in said cream formulation is generally in a weight range of between about 0.6 gram and about 1.0 gram.

6. A cream formulation for topical application to an external portion of a human body, according to claim 1, wherein said predetermined weight of said vitamin E present in said cream formulation is generally in a weight range of between about 1000 IU and about 3000 IU.

7. A cream formulation for topical application to an external portion of a human body, according to claim 1, wherein said predetermined weight of said vitamin E present in said cream formulation is generally in a weight range of between about 7000 IU and about 9000 IU.

8. A cream formulation for topical application to an external portion of a human body, according to claim 1, wherein said predetermined weight of said purified extract of said leaves of said plant *Eriobotrya japonica* present in said cream formulation is generally in a weight range of between about 6 mg and about 12 mg.

9. A cream formulation for topical application to an external portion of a human body, a one ounce preparation of such cream formulation includes active ingredients consisting essentially of:
   (a) a predetermined weight of an aloe vera gel compound, said predetermined weight of said aloe vera gel compound being present in said cream formulation generally in a weight range of between about 3 grams and about 10 grams;
   (b) a predetermined weight of a preselected zinc compound, said predetermined weight of said preselected zinc compound being present in said cream formulation generally in a weight range of between about 0.4 gram and about 1.5 grams;
   (c) a predetermined weight, expressed as IU, of vitamin E, said predetermined weight of said vitamin E being present in said cream formulation generally in a weight range of between about 200 IU and about 9000 IU;

(d) a predetermined weight of a very pure extract from leaves of a plant *Eriobotrya japonica,* said predetermined weight of said very pure extract from said leaves of said plant *Eriobotrya japonica* being present in said cream formulation generally in a weight range of between about 100 micrograms and about 600 micrograms; and (e) a balance of said one ounce preparation of said cream formulation being made up of water, organic solvents, carriers and emollients.

* * * * *